US008263351B2

(12) United States Patent
Jackowski et al.

(10) Patent No.: US 8,263,351 B2
(45) Date of Patent: Sep. 11, 2012

(54) DIAGNOSTIC METHODS FOR CONGESTIVE HEART FAILURE

(75) Inventors: George Jackowski, Kettleby (CA); Tracy Van Lieshout, Hamilton (CA); Brad Thatcher, Casalnuovo de Napoli (IT); Rulin Zhang, Brampton (CA); Jason Yantha, Toronto (CA); Michele Rasamoelisolo, Winnipeg (CA)

(73) Assignee: Nexus DX, Inc., San Diego, CA (US)

( * ) Notice: Subject to any disclaimer, the term of this patent is extended or adjusted under 35 U.S.C. 154(b) by 0 days.

(21) Appl. No.: 13/024,963

(22) Filed: Feb. 10, 2011

(65) Prior Publication Data

US 2011/0183436 A1    Jul. 28, 2011

Related U.S. Application Data

(60) Division of application No. 11/786,885, filed on Apr. 13, 2007, now abandoned, which is a continuation of application No. 10/706,599, filed on Nov. 11, 2003, now abandoned.

(51) Int. Cl.
*G01N 33/53* (2006.01)
(52) U.S. Cl. ........................................ 435/7.1; 436/518
(58) Field of Classification Search ........................ None
See application file for complete search history.

(56) References Cited

U.S. PATENT DOCUMENTS

| 4,208,479 | A | 6/1980 | Zuk et al. |
| 6,190,691 | B1 | 2/2001 | Mak |
| 6,572,895 | B2 | 6/2003 | Smith |

OTHER PUBLICATIONS

Claster et al., "Degradation of Erythrocyte Glycophorin Results in Increased Membrane bound Hemoglobin", Archives of Biochemistry and Biophysics, vol. 285, No. 1, Feb. 15, 1991, pp. 147-152.
Communication pursuant to Article 94(3) EPC, dated Aug. 27, 2009, issued in connection with corresponding European application No. 04797198.1-1223.
Elliott et al. (J. Immunological Method 1998 vol. 217 p. 121-130).
B. Goldman et al "Hematopoiesis/erythropoiesis in myocardial infarcts", Modem Pathology, 14(6):589-594 (2001).
G. Caimi et al, "Erythrocyte aggregation and erythrocyte membrane properties in Type 2 Diabetes mellitus and in vascular atherosclerotic disease", Thromb Haemost, 83:516-517 (2000).
H. Demiroglu et al, "Enhanced erythrocyte aggregation in Type 2 Diabetes with late complications", Experimental Clinical Endocrinol Diabetes, 107(1):35-39 (1999).
E. Eylar et al, "The contribution of sialic acid to the surface charge of the erythrocyte", The Journal of Biological Chemistry, 237(6):1992-2000 (1962).
M. Gaczynska et al, "Abnormal degradation of red cell membrane proteins in diabetes", Cytobios, 75:7-11 (1993).
B. Names et al, "Antibodies as tools", Instant Notes: Biochemistry, 2nd edition, Springer-Verlag, New York, pp. 112-114 (2000).
B. Names et al, "Integral membrane proteins", Instant Notes: Biochemistry, 2nd edition, Springer-Verlag, New York, pp. 125, 126, and 130 (2000).
M. Martinez et al, "Alterations in erythrocyte aggregability in diabetics: the influence of plasmatic fibrinogen and phospholipids of the red blood cell membrane", Clinical Hemorheology and Microcirculation, 18:253-258 (1998).
A. Piwowar et al, "Concentration of leukocyte elastase in plasma and polymorphonuclear neutrophil extracts in type 2 diabetes", Clinical Chemistry Lab Medicine, 38(12):1257-1261 (2000).
M. Rasamoelisolo et al, "Fine characterization of a series of new monoclonal antibodies directed against glycophorin A", Vox Sanguinis, 72:185-191 (1997).
M. Rogers et al, "Decrease in erythrocyte glycophorin sialic acid content is associated with increased erythrocyte aggregation in human diabetes", Clinical Science, 82:309-313 (1992).
A. Santos-Silva et al, "Erythrocyte damage and leukocyte activation in ischemic stroke", Clinica Chimica Acta, 320:29-35 (2002).
T. Scott et al, "Erythrocyte membrane", Concise Encyclopedia: Biochemistry and Molecular Biology, 3rd edition, revised and expanded, Walter de Gruyter, Berlin-New York, pp. 201-202 (1997).
L. Solang et al, "Diabetes mellitus and congestive heart failure", European Heart Journal, 20:789-795 (1999).
B. Venerando et al, "Acidic and neutral sialidase in the erythrocyte membrane of Type 2 diabetic patients", Blood, 99(3):1064-1070 (2002).
M. Wegner et al, "Role of neutral endopeptidase 24.11 in AV distular rat model of heart failure", Cardiovascular Research, 31:891-898 (1996).
O. Ziegler at al, "Increased erythrocyte aggregation in insulin-dependent diabetes mellitus and its relationship to plasma factors: a multivariate analysis", Metabolism, 43(9):1182-1186 (1994).

*Primary Examiner* — Jacob Cheu
(74) *Attorney, Agent, or Firm* — Cooley LLP

(57) ABSTRACT

The invention provides an assay for the quantification of circulating glycophorin in biological fluid samples. The circulating glycophorin measured by this assay is a truncated glycophorin diagnostic for congestive heart failure (CHF).

7 Claims, 8 Drawing Sheets

DIAGNOSTIC METHODS FOR CONGESTIVE HEART FAILURE

CROSS REFERENCE TO RELATED APPLICATION

This application is a divisional of U.S. patent application Ser. No. 11/786,885, filed Apr. 13, 2007, which is a continuation of U.S. patent application Ser. No. 10/706,599, filed on Nov. 11, 2003, the contents of which are all incorporated herein by reference.

FIELD OF THE INVENTION

Description Of The Text File Submitted Electronically

The contents of the text file submitted electronically herewith are incorporated herein by reference in their entirety: A computer readable format copy of the Sequence Listing (filename: NEXU _023_02US _SubSeqlist.txt, date recorded: Mar. 30, 2011, file size 7kilobytes).

The instant invention relates generally to the field of immunology; particularly to the use of immunologic assays to diagnose abnormal or disease states and most particularly to a sandwich ELISA (enzyme-linked immunosorbent assay) assay for the quantification of a truncated glycophorin circulating in biological fluid which is diagnostic for congestive heart failure (CHF).

BACKGROUND OF THE INVENTION

The diagnosis of a given disease requires standard agreed-upon observations usually made by the attending physician of the sick patient. For some diseases, a single test is available which gives nearly definitive results sufficient for a correct diagnosis, for example, the glucose tolerance test for diabetes. However, most diseases require a number of sophisticated tests to arrive at a probable diagnosis. At the present time, therapeutic interventions are frequently initiated at late stages of disease, often resulting in only modest improvements in the quality and length of the affected patients life. Disease prevention is easier and more effective than disease therapy. Earlier diagnosis decreases disease-associated morbidities, increases the quality and length of life of the patient and decreases overall costs of health care. Thus, it is a goal of biomedical researchers to develop diagnostic tests which can correctly diagnose disease at the early stages.

Early diagnosis of congestive heart failure (CHF) is particularly beneficial since the cardiac re-structuring which occurs with progressive disease may be slowed or prevented with early therapeutic intervention. However, early diagnosis has proven elusive since symptoms generally do not appear until the heart has already suffered structural changes.

CHF is a serious condition with a high mortality rate affecting approximately five million Americans (see U.S. Pat. No. 6,572,895 for a discussion of CHF). It is currently believed that CHF is not a distinct disease process in itself, but rather represents the effect of multiple abnormalities which interact together to ultimately produce the progressive loss of the ability of the heart to function as a circulatory pump. Major pathophysiologic abnormalities which occur in CHF are activation of the hypothalmic-pituitary-adrenal axis, systemic endothelial dysfunction and myocardial re-structuring. The progression of CHF can be initiated by an event such as myocardial infarction wherein the heart muscle is damaged or it can result from hypertension and/or cardiac malformations.

Recently, it has been discovered that patients with certain conditions such as insulin resistance and Type II diabetes have a particularly high risk for heart failure and poor prognosis once they develop CHF (Solang et al. European Heart Journal 20:789-795 1999).

Disease processes, such as those which occur in diabetes and CHF, often result in cellular and/or tissue damage followed by the release of cellular and/or tissue specific biopolymer markers into the bodily fluids of an individual. These biopolymer markers are harbingers of disease and/or disease progression. Association of such biopolymer markers with abnormal and/or disease states provides new diagnostic avenues which may allow identification of patients in the early stages of disease or patients at risk for developing disease. Identification of biopolymer markers diagnostic for CHF is particularly advantageous considering the progressive pathophysiology involved in CHF. What is lacking in the art is an efficient, easy to perform diagnostic method capable of identifying an individual suffering from CHF.

SUMMARY OF THE INVENTION

The instant invention' provides an efficient, easy to perform diagnostic method capable of identifying an individual suffering from CHF. The method comprises a sandwich ELISA assay using mouse monoclonal antibodies (anti-glycophorins) to quantify elevated glycophorin in biological fluids. Glycophorin is the major integral membrane protein of the mammalian red blood cell (RBC) and is highly glycosylated. The glycosylation of glycophorin is responsible for the overall negative charge of the RBC cellular surface leading to the normal electrostatic repulsion among red blood cells. In the disease processes of diabetes and CHF the red blood cell (RBC) membrane proteins, including glycophorins, are abnormally degraded, thus reducing the overall negative charge of the cellular surface leading to a decrease in the normal electrostatic repulsion among red blood cells. As a consequence, aggregation of red blood cells occurs in the pathogenesis of diabetes and CHF. Using the sandwich ELISA assay of the invention, the instant inventors identified an abnormal, circulating glycophorin in the plasma of CHF patients. This glycophorin had a lower molecular weight than that of normal glycophorin, thus it is predicted to be a truncated fragment which has been cleaved from the RBC membrane surface during the disease process.

Three mouse monoclonal antibodies are used in the ELISA assay of the instant invention; 3F4, 6G4 and 5F4. Monoclonal antibody 3F4 recognizes amino acid residues 5-25 of SEQ ID NO:2 and SEQ ID NO:4 (glycophorins A and B). Monoclonal antibody 6G4 recognizes amino acid residues 39-45 of SEQ ID NO:2 (glycophorin A). Monoclonal antibody 5F4 recognizes amino acid residues 107-119 of SEQ ID NO:2 (glycophorin A).

Accordingly, it is an objective of the instant invention to provide a sandwich ELISA assay using mouse antiglycophorin monoclonal antibodies 3F4, 6G4 and 5F4 for the quantification of an abnormal, truncated glycophorin circulating in biological fluid.

It is another objective of the instant invention to identify a circulating, truncated glycophorin diagnostic for congestive heart failure (CHF).

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 5A shows captured glycophorin from CHF patients; FIG. 5B shows captured glycophorin from healthy patients and FIG. 5C shows captured purified glycophorin.

DEFINITIONS

Figure 1:
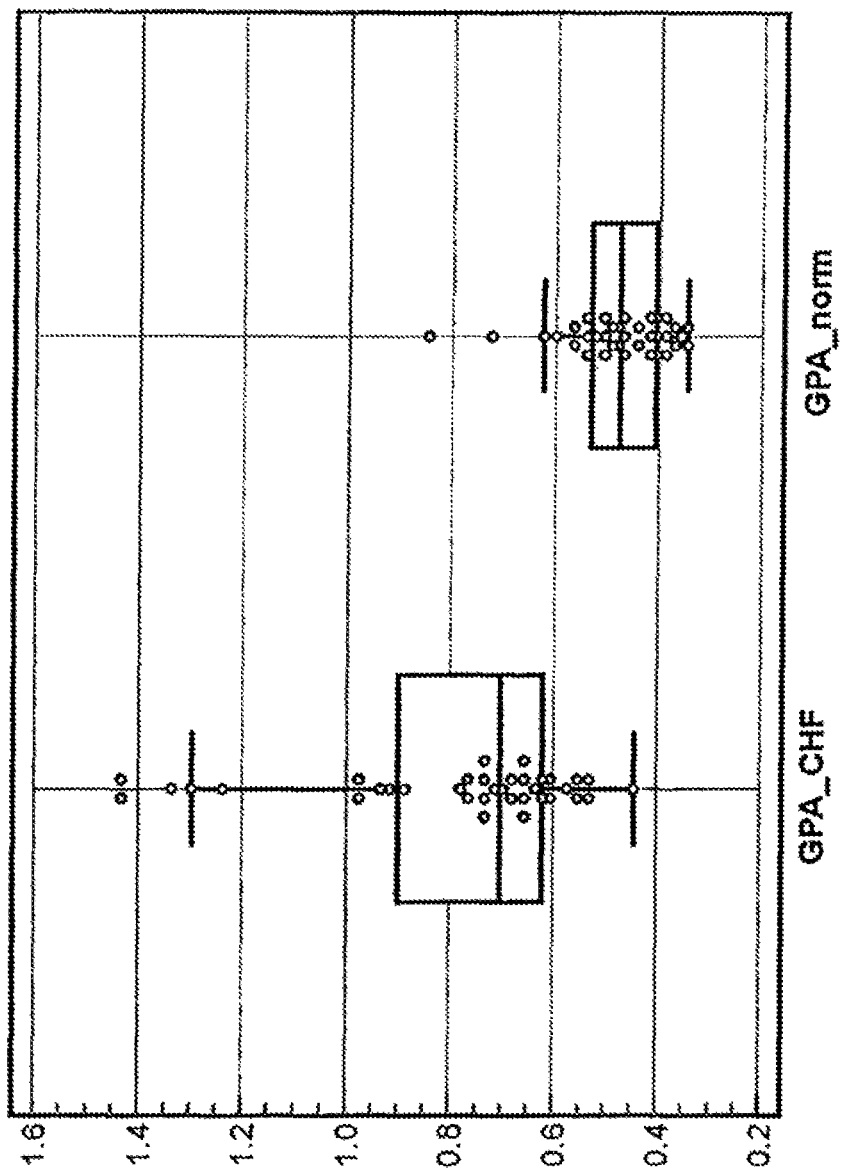
FIG. 1 shows the data resulting from the sandwich ELISA using monoclonal antibody 3F4.

The following list defines terms, phrases and abbreviations used throughout the instant specification. Although the terms, phrases and abbreviations are listed in the singular tense the definitions are intended to encompass all grammatical forms.

As used herein, the abbreviation "CHF" refers to congestive heart failure.

As used herein, the abbreviation "GP" refers to glycophorin.

As used herein, the abbreviation "GPA" refers to glycophorin A.

As used herein, the abbreviation "GPB" refers to glycophorin B.

As used herein, the abbreviation "GPAx2" refers to the dimerized form of glycophorin A.

As used herein, the abbreviation "GPBx2" refers to the dimerized form of glycophorin B.

As used herein, the abbreviation "ELISA" refers to enzyme-linked immunosorbent assay.

As used herein, the abbreviation "RBC" refers to red blood cell.

As used herein, the abbreviation "MoAb" refers to monoclonal antibody.

As used herein, the abbreviation "MS" refers to mass spectrometry.

As used herein, the abbreviation "SELDI" refers to a mass spectrometric technique; surface enhanced laser desorption ionization.

As used herein, the abbreviation "PBS" refers to phosphate buffered saline.

The terms "RBC", "red blood cell" and "erythrocyte" are used interchangeably herein.

As used herein, the term "glycophorin" refers to the major integral glycoprotein of the mammalian erythrocyte membrane. Glycophorin is highly glycosylated and occurs in isoforms A and B (see Concise Encyclopedia: Biochemistry and Molecular Biology, Third Edition, Revised and Expanded by Thomas A. Scott and E. Ian Mercer, Walter de Gruyter, Berlin-New York 1997, pages 201-202 and Instant Notes: Biochemistry, 2nd edition, B. D. Hames and N. M. Hooper, Springer-Verlag New York 2000, pages 125, 126 and 130 for an introduction to the RBC membrane and glycophorins).

As used herein, the term "circulating, truncated glycophorin" refers to the abnormal glycophorin fragment identified by the assay of the instant invention in the serum of CHF patients. The 3F4 mouse anti-glycophorin monoclonal antibody which recognizes the extracellular portion of glycophorin A and B binds to this circulating, truncated glycophorin. This circulating, truncated glycophorin is structurally different from the normal soluble glycophorin and is theorized to be a fragment cleaved from the RBC surface during disease processes.

As used herein, the term "biological fluid" refers to any bodily fluid. Illustrative, albeit non-limiting examples are blood, blood products, urine, saliva, cerebrospinal fluid and lymphatic fluid.

As used herein, the term "subject" refers to any mammalian organism. A particularly preferred subject is a human.

As used herein, the term "corresponding" is used generally with reference to antibody-antigen binding complexes, for example, an antibody corresponding to an antigen will bind to the antigen under physiologic conditions. The bound antibody-antigen is referred to as an antibody-antigen binding complex.

As used herein, the term "signal generating substance" refers to any material which undergoes a measurable reaction. Illustrative, albeit non-limiting examples are fluorophores, enzymes and radioisotopes. A particularly preferred signal generating substance is peroxidase, the use of which is illustrated in the examples herein.

As used herein, the term "congestive heart failure" refers to a progressive, debilitating condition wherein the heart loses its ability to function as a circulatory pump.

As used herein, the term "antibody" refers to a protein secreted by B lymphocytes capable of binding specific molecules under physiologic conditions.

As used herein, the term "monoclonal antibody" refers to an antibody having single epitope specificity.

As used herein, the term "polyclonal antibody" refers to an antibody capable of binding with multiple epitopes.

As used herein, the term "antigen" broadly refers to any substance which induces an immune reaction; more particularly the term "antigen" refers to the corresponding binding partner of an antibody.

As used herein, the term "auto-antibody" refers to an antibody which recognizes self antigens, for example, antibodies produced by an organism which bind the organism's own proteins are referred to as auto-antibodies.

Specific antibodies can be used to quantify the amount of corresponding antigen in a biological sample. As used herein, the term "ELISA" refers to an enzyme-linked immunosorbent assay which can quickly detect and quantify minute amounts (less than a nanogram) of antigen in a biological sample. The test antibody is bound to an inert polymer support, such as a plastic tray with molded wells, and then exposed to the biological sample. Unbound proteins are washed away and a second antibody that reacts with the antigen at a different epitope than the test antibody reacts with is added. This second antibody has an enzyme attached to it that converts a colorless or nonfluorescent substrate into a colored or fluorescent product. The amount of second antibody bound, and hence the amount of protein antigen present in the original biological sample, is determined by the quantification of the intensity of color or fluorescence produced. This ELISA assay is also referred to as an "indirect ELISA" or a "sandwich ELISA". (see Instant Notes: BioChemistry, 2nd edition, B. D. Hames and N. M. Hooper, Springer-Verlag New York 2000, pages 112-114 for an introduction to the general principles of ELISA assays). There is also a form of ELISA assay that is referred to as "direct" wherein the antigen is bound to an inert polymer support and exposed to a biological sample containing the corresponding antibody.

DETAILED DESCRIPTION OF THE INVENTION

As a result of disease processes, damage to cells and tissues of the body occurs at the cellular and sub-cellular levels. Initially, these processes may only cause damage to the outer membranes of cells, causing a sloughing off of portions of the exterior cellular matrices, which process is broadly defined as reversible damage. As the length of time and/or the severity of the disease condition increases, the outer membranes begin to break down, resulting in membrane rupture followed by the release of intra-cellular components, which process is broadly defined as irreversible damage. When such damage occurs (reversible or irreversible), biopolymer markers are released into the circulation, causing the immune system to become activated, since these biopolymer markers are not normally present in the bodily fluids. The immune system views these biopolymer markers as invading pathogens or foreign bodies whose threat must be neutralized. In an effort to persevere against this perceived threat, auto-antibodies are formed to these biopolymer markers. These auto-antibodies can be characterized as sequela which are indicative of the original damaging insult to the organism. The presence of the auto-antibodies validates the theory that cellular damage acts as an initiator of an immune response leading to a cascade of auto-antibody production which ultimately manifests itself in a characteristic and often predictable disease state. The appearance of these biopolymer markers and their associated auto-antibodies are harbingers of disease and/or disease progression and are useful for diagnostic purposes.

Damage to the red blood cell membrane is known to occur in disease processes such as diabetes and CHF. In these diseases there is an increase in enzyme production and/or activation (neutrophil proteases, metalloproteases, sialidases and endopeptidases) that directly and/or indirectly leads to abnormal degradation of red blood cell membrane proteins (Gaczyfiska et al. Cytobios 75:7-11 1993; Venerando et al. Blood 99(3):1064-1070 2002; Wegner et al. Cardiovascular Research 31:891-898 1996; Piwowar et al. Clinical Chemistry Lab Medicine 38(12):1257-1261 2000 and Santos-Silva et al. Clinica Chimica Acta 320:29-35 2002).

Additionally, it is well-documented that erythrocyte (RBC) aggregability is increased in diabetes and in vascular atherosclerotic disease (Caimi et al. Thromb Haemost 83:516-517 2000; Demiroglu et al. Experimental Clinical Endocrinol Diabetes 107(1):35-39 1999; Martinez et al. Clinical Hemorheology and Microcirculation 18:253-258 1998 and Ziegler et al. Metabolism 43(9):1182-1186 1994). Alterations in RBC membrane phospholipids are associated with RBC aggregability (Martinez et al. Clinical Hemorheology and Microcirculation 18:253-258 1998). Sphingomyelin is the main phospholipid of the outer membrane and has been shown to contain a greater percentage of saturated fatty acids in diabetic patients than in non-diabetic patients. This increase in saturation is thought to reduce electrostatic repulsion between red blood cells, which in turn increases their aggregability.

Loss of glycophorins further reduces the electrostatic repulsion of red blood cells. Glycophorin is the major RBC integral membrane glycoprotein. The high sialylation of glycophorin is responsible for the negative surface charge which leads to the normal electrostatic repulsion between red blood cells (Eylar et al. The Journal of Biological Chemistry 237 (6):1992-2000 1962). The increase in enzyme production and/or enzyme activation in disease processes such as diabetes results in the loss of glycophorins from the RBC membrane. These glycophorin fragments are released into the bodily fluids where they stimulate the production of auto-antibodies. The decrease in glycophorin in turn leads to a decrease in the normal negative charge of the RBC membrane surface and thus decreases the overall electrostatic repulsion between blood cells. Loss of the electrostatic repulsion between red blood cells results with the aggregation of red blood cells seen in diabetes.

Without being bound by any particular theory, the instant inventors propose that the circulating, truncated glycophorin identified in the plasma of CHF patients using the sandwich ELISA assay described herein is an extracellular glycophorin fragment which has been cleaved from the RBC membrane during the disease process. This circulating, truncated glycophorin is structurally different from the normal soluble form of glycophorin. The mouse anti-glycophorin 3F4 monoclonal antibody which recognizes amino acid residues 5-25 of SEQ ID NO:2 and SEQ ID NO:4 (glycophorins A and B) also recognizes the circulating, truncated glycophorin. The instant inventors have also shown by direct ELISA assay that CHF patients show an increase in anti-glycophorin auto-antibodies. Thus, it is concluded that this circulating, truncated glycophorin can be used as a new biopolymer marker for CHF diagnosis.

Experimental Procedures

Sequences

Homo sapiens (human) glycophorin A nucleic acid sequence is disclosed as SEQ ID NO:1 and translates into glycophorin A protein disclosed as amino acid sequence SEQ ID NO:2. Homo sapiens (human) glycophorin B nucleic acid sequence is disclosed as SEQ ID NO:3 and translates into glycophorin B protein disclosed as amino acid sequence SEQ ID NO:4.

Antibodies

The mouse anti-glycophorin monoclonal antibodies used in the following experiments were purchased from BioAtlantic (Nantes Cedex, France). Monoclonal antibody 6G4 recognizes amino acid residues 39-45 of SEQ ID NO:2 (glycophorin A). Monoclonal antibody 5F4 recognizes the intracellular portion of glycophorin A comprising amino acid residues 107-119 of SEQ ID NO:2. Monoclonal antibody 3F4 recognizes the extracellular portion of glycophorins A and B amino acid residues 5-25 of SEQ ID NO:2 and SEQ ID NO:4. The binding of the 3F4 antibody to its epitope is sugar-dependent whereas the binding of the 6G4 antibody is not. These monoclonal antibodies are described in detail in Rasamoelisolo et al. Vox Sanguinis 72:185-191 1997.

The mouse anti-glycophorin 3F4 monoclonal antibody was deposited with the American Type Culture Collection (ATCC) on Apr. 23, 2000 as hybridoma NaM26-3F4D11A2 under Accession number PTA-5154. The American Type Culture Collection (ATCC) is located at 10801 University Boulevard, Manassas, Va. 20110-2209. Applicants submit that all restrictions on the availability to the public of this deposited material will be irrevocably removed upon granting of a patent in the United States.

Quantification of Glycophorin by Sandwich ELISA

One ug of each MoAb in 100 ul of 50 mM carbonate pH 9.4 was coated on ELISA plates (Nuc, Denmark) and set overnight at +4° C. Plates were then washed 3 times with 0.01M phosphate buffer 150 mM NaCl pH 7.4 (PBS) purchased from Sigma containing 0.05% Tween 20 (PBST). Plates were then blocked with 200 ul of PBST containing 0.5% BSA (Sigma) for 30 minutes at 37° C. 100 ul of CHF patient plasma (PRAISE 2 study) and healthy control plasma (Intergen)

diluted 1/10 in PBST were then added per well in duplicate and incubated for 2 hours at room temperature. After 3 washes with PBST, 100 ul of rabbit polyclonal anti-glycophorin A+B (BioAtlantic) were added and incubated for 1 hour at room temperature followed by the addition of 100 ul of peroxidase labeled donkey polyclonal anti-rabbit IgG (H+L) diluted 1/50,000 in PBST containing 0.5% BSA (Jackson ImmunoResearch). The presence of the captured glycophorins is detected by adding 100 ul of TMB (Moss, Inc.). The reaction was stopped with 50 ul of 1N $H_2SO_4$. Plates were then read at 450 nm on the BioRad microplate reader.

FIG. 1 shows the result of the sandwich ELISA using the 3F4 monoclonal antibody. The absorbance at 450 nm is shown on the Y axis. Glycophorin captured from the plasma of CHF patients is shown on the left and the glycophorin captured from normal plasma (control, n=36) is shown on the right. The signal is significantly higher in CHF plasma than in controls (p<0.001) calculated by an independent t-test indicating a higher amount of glycophorins in CHF plasma samples. The 3F4 MoAb recognizes the common sequence on both glycophorins A and B (amino acid residues 5-25 of SEQ ID NO:2 and SEQ ID NO:4). This binding is sugar-dependent since this fragment of glycophorin is highly glycosylated.

In order to ascertain whether the assay is specific to the extracellular polypeptide of glycophorin or the oligosaccharide chains, the MoAbs 6G4 (recognizes amino acid residues 39-45 of SEQ ID NO:2) and 5F4 (recognizes amino acid residues 112-129 of SEQ ID NO:2) were used. Both bind to the glycophorin A backbone independently of the sugar chains.

Figure 2:
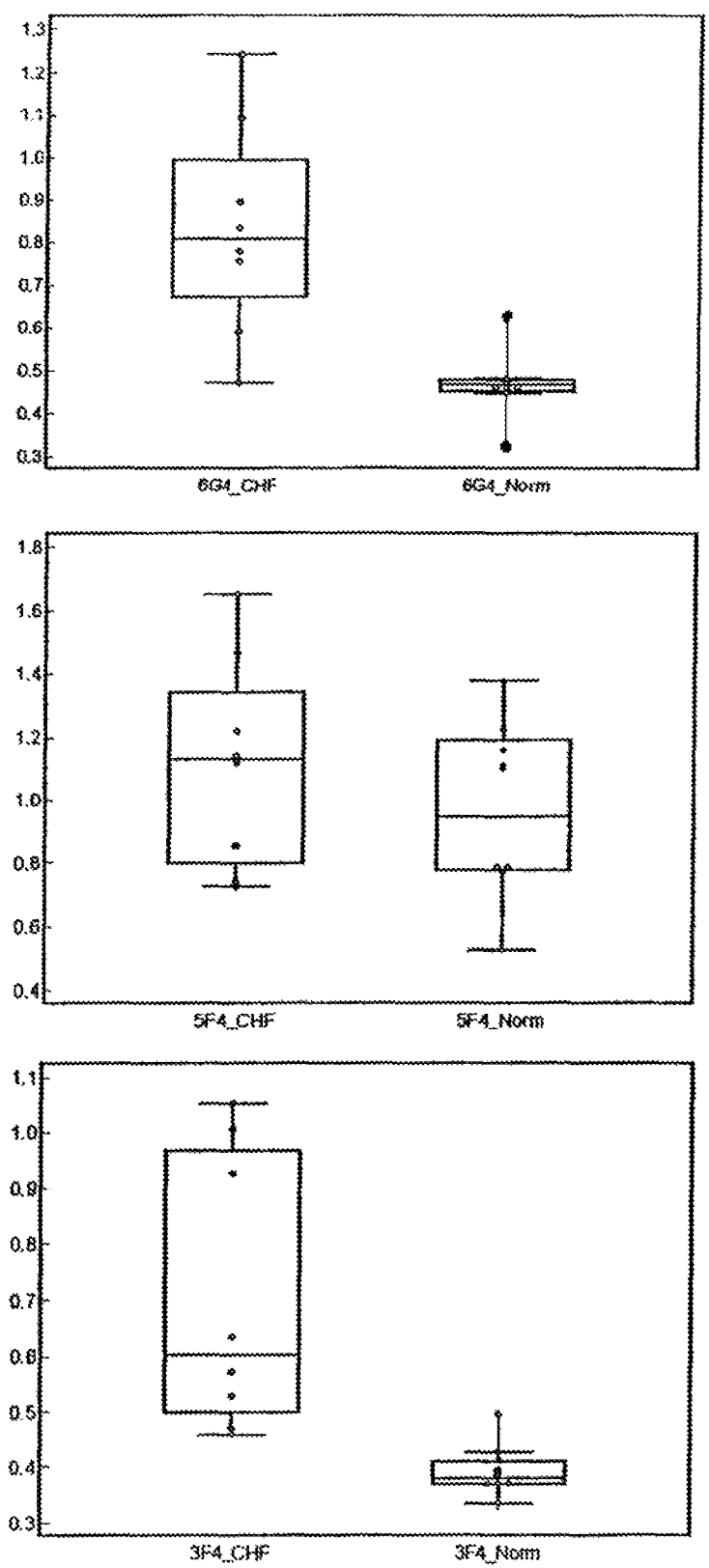
FIG. 2 shows the data resulting from the sandwich ELISA using monoclonal antibodies 6G4, 5F4 and 3F4.

Eight CHF samples having the most elevated amount of glycophorin and 8 normal plasma samples having the lowest amount of glycophorin were analyzed and the result is shown in FIG. 2. FIG. 2 shows results from sandwich ELISA assays comparing the glycophorin captured in plasma from CHF patients and the glycophorin captured in normal control plasma (n=8). The top panel shows results using the 6G4 MoAb (p=0.001); the middle panel shows results using the 5F4 MoAb (p=0.36) and the bottom panel shows the results using the 3F4 MoAb (p=0.003). The Y axis represents the absorbance read at 450 nm Glycophorin captured from the plasma of CHF patients is shown on the left and the glycophorin captured from normal plasma is shown on the right in all three panels. The result shows that 6G4 detects elevated amount of glycophorin in CHF samples, while 5F4 shows no significant difference between both CHF and normal human plasma. This result indicates that glycophorin may be cleaved from the red blood cell membrane during the progression of CHF since the fragments recognized by the antibodies are extracellular fragments. However, it is noted that a soluble form of glycophorin is present in normal as well as CHF patient plasma that is detected by the 5F4 monoclonal anti-intracellular domain of glycophorin.

Detection of Auto-Antibody by Direct ELISA 0.5 ug of purified glycophorin from blood group MM or asialoglycophorins from blood group MN (Sigma) in 50 mM carbonate buffer pH 9.4 was adsorbed onto ELISA plates overnight at +4° C. Plates washed 3 times with 0.01M Phosphate buffer 150 mM NaCl Ph 7.4 (PBS) from Sigma containing 0.05% Tween 20 (PBST). Plates were then blocked with 200 ul of PBST containing 0.5% BSA (Sigma) for 30 minutes at 37° C. 100 ul of CHF plasma (PRAISE 2 study) and normal control plasma (Intergen) diluted 1/100 in PBST were then added per well in duplicate and incubated for 2 hours at room temperature. After 3 washes with PBST, 100 ul of peroxidase labeled goat polyclonal anti-human IgG (H+L) diluted 1/10,000 in PBST (Jackson ImmunoResearch) were added. The presence of auto-antibody anti-glycophorins was detected by adding 100 ul of TMB (Moss, Inc.) and the reaction was stopped with 50 ul of 1N H2SO4. Plates were read at 450 nm on the BioRad microplate reader.

Glycophorin is known to be highly immunogenic due to the presence of a high amount of sugar chains. Once found in plasma it may induce an immune response generating antiglycophorin auto-antibody.

Figure 3:
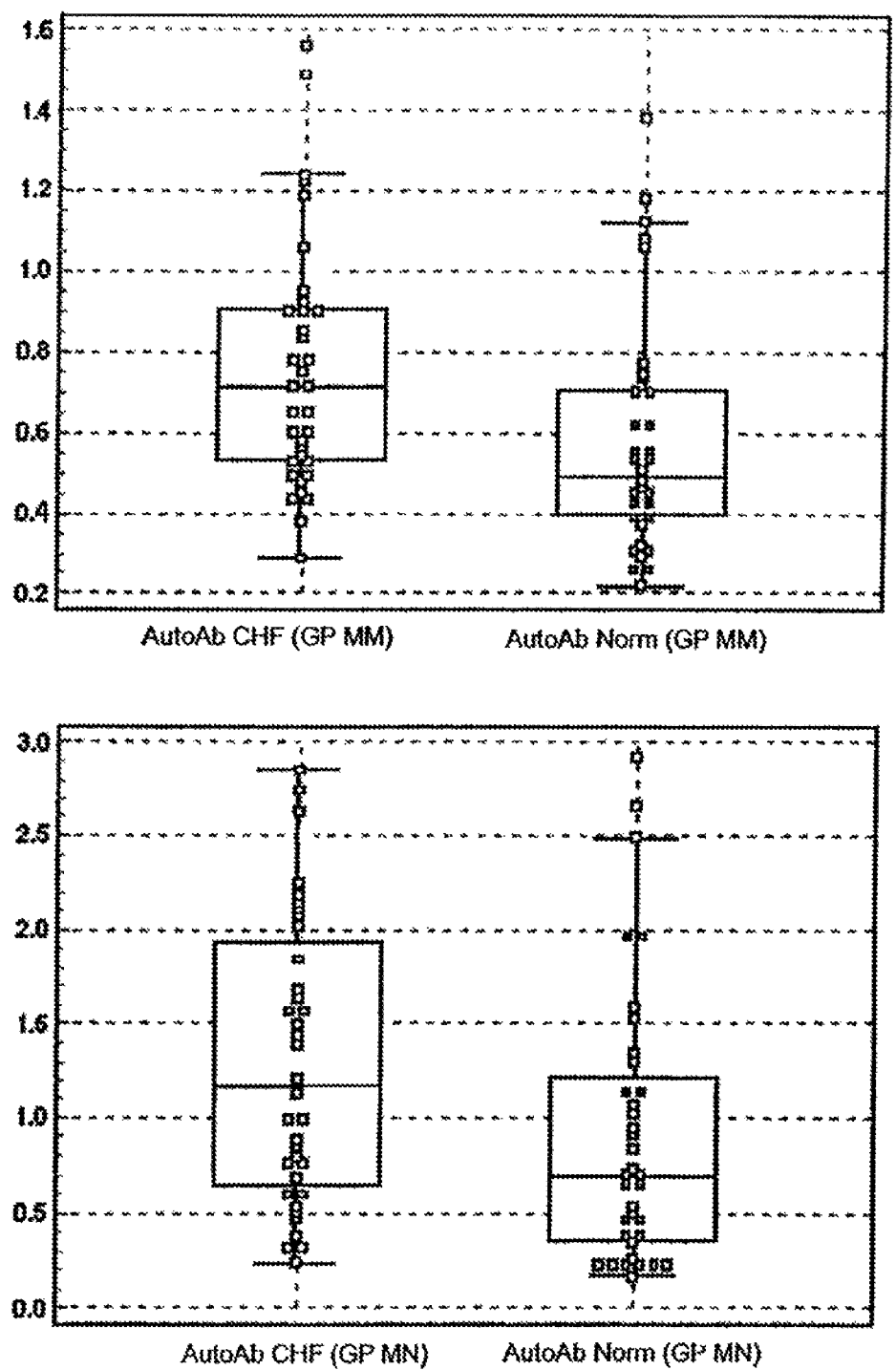
FIG. 3 shows the data resulting from the direct ELISA evaluating the presence of an autoantibody to glycophorin.

To demonstrate the presence of CHF-induced auto-antibody against glycophorin, glycophorins from blood group MM and asialo glycophorins from blood group MN were coated on ELISA plates and plasma from healthy donors or from CHF patients were added. FIG. 3 shows the results of the direct ELISA assay evaluating the presence of a CHF-induced auto-antibody in the plasma of normal and CHF patients (n=36). In the top panel, glycophorin from blood group MN was coated on the plate (p=0.01) and the bottom panel, desialylated glycophorin from blood group MN was coated on the plate (p=0.03). The Y axis represents the absorbance read at 450 nm FIG. 3 shows the presence of auto-antibodies in CHF; independent to the blood group (M or N) and the heavy sialic acids on glycophorin.

Identification of Glycophorins in CHF Plasma by Immunoprecipitation and Detection by Immunoblotting 1.2 ml of pooled CHF plasma from the PRAISE 2 study was diluted v/v with PBS containing 0.5% Triton X-100. Then 2 ul of 3F4 MoAb at 1.7 mg/ml were added. After overnight incubation at +4° C., 25 ul of goat IgG anti-mouse IgG (H+L) coupled to SEPHAROSE-4B beads (Zymed) were added. The mixture was incubated for 5 hours at +4'C and then the beads were washed 3 times with PBS containing 0.05% Tween 20. The captured (glyco)protein was eluted with 100 ul of 0.1M glycine pH 2.5 then neutralized with 1M Tris pH 11. The eluate was concentrated on CentriVap Concentrator (Labconco), resuspended in 50 ul of SDS-PAGE sample buffer, boiled 5 minutes at 100° C. and then loaded on 10% SDS-PAGE gel. At the end of the electrophoresis, proteins were transferred onto a nitrocellulose membrane and stained with 3F4 MoAb anti-GPA+B followed by a peroxidase labeled goat polyclonal anti-mouse IgG (H+L) diluted 1/50,000 in PBST (Jackson ImmunoResearch). The immunoblot was then developed using ECL (Amersham Pharmacia). To control the cross-reactivity of the secondary antibody to the 3F4 eluted from the column, the blot was incubated with the secondary antibody alone.

Figure 4:
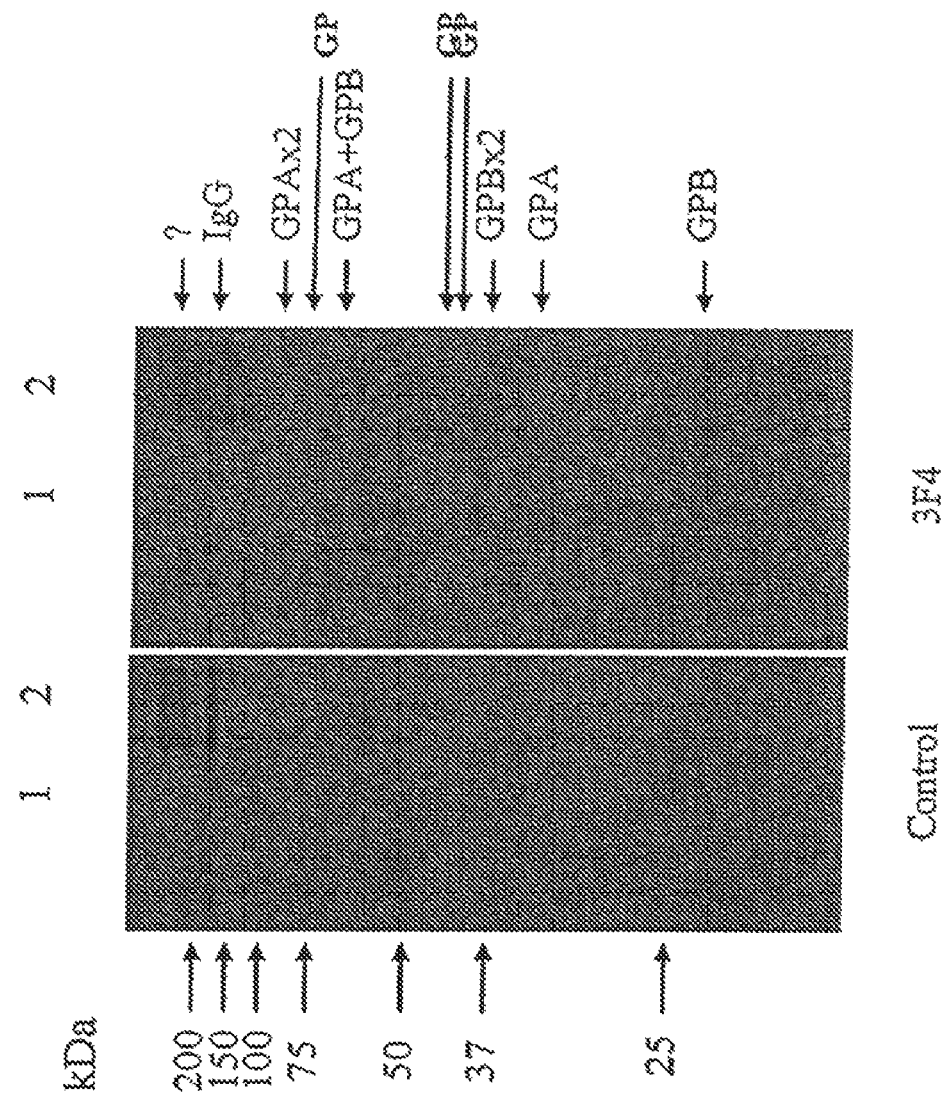
FIG. 4 shows the results of immunoprecipitation of glycophorin from the plasma of CHF patients.

The molecules captured by 3F4-column were eluted and loaded on 10% SDS-PAGE gel and assessed on immunoblotting against the same MoAb. As shown in FIG. 4, the glycophorins found in CHF plasma have a molecular weight of 75, 45 and 40 kDa (lane 2, blot incubated with 3F4). Usually glycophorins run at 80-70-40-37 and 20 kDa as dimer form of GPA, dimer GPA/GPB, dimer form of GPB, monomer form of GPA and monomer form of GPB, respectively as shown on lane 1 loaded with normal glycophorin purified from normal red blood cell membrane. Thus, the glycophorins found in the plasma of CHF patients have different molecular weights as compared to the normal glycophorin purified from RBC membranes. The immunoblot was incubated with the secondary antibody alone (control) or with the 3F4 antibody and then the secondary antibody. Lane 1 (in both blots) shows glycophorin purified from RBC membranes and Lane 2 (both blots) shows glycophorin from CHF patient plasma. Protein markers from 25 to 200 kDaltons are shown on the far left.

The IgG identified in control and 3F4 blots is the mouse monoclonal 3F4 used for the immunoprecipitation and released from the column. A band with a high MW>200 kDa is also detected. The instant inventors are not sure about the nature of this band. The band may be a complex form of IgM or IgG autoantibodies and the glycophorins.

Identification of Glycophorin in CHF Patient Sample by SELDI-TOF

The method of the instant invention can be carried out using the techniques of mass spectrometry. The PS20 chip (Ciphergen) was washed with pure Acetonitrile-190 (ACN) (Caledon) and allowed to air dry. 50 gg of Protein G (Pierce) was dissolved in 50 gl UF water and 1 ul was loaded to each spot containing 1 gl of ACN. The mixture was incubated 1 hour in a humidity chamber and then the spot was blocked with 10 gl of 0.5M Tris-HCl pH 7.4 (Caledon) for 15 minutes. The chip was then washed with UF water and allowed to air dry. Monoclonal antibody (MoAb) anti-GPA+GPB, the 3F4 at 1.7 mg/ml (BioAtlantic) was diluted 1/3 in PBS containing 0.1% TRITON X (Sigma) and 3 gl of the MoAb solution was loaded per spot and incubated for 1 hour in a humidity chamber. Unbound MoAb was washed away from the chip by washing with PBS.

Purified glycophorin (Sigma), CHF plasma from PRAISE 2 study or normal plasma (Intergen) was added to the 3F4-coated chip as follows:

The glycophorin at 1 mg/ml was diluted 1/5 in PBS; CHF and normal plasma samples were diluted 1/5 in PBS containing 0.05% Tween 20, and 2 gl of each were loaded per spot. The chip was then incubated for 1 hour in a humidity chamber and washed twice with UF water.

The captured glycophorin was then treated with Endoproteinase G1uC (Roche Diagnostics). For that, the G1uC powder was dissolved in 50 gl of UF water and a 1/10 dilution in 50 mM Ammonium Carbonate pH 7.8 (BDH Laboratory Supplies) was prepared. 11.0 of the GluC solution was added to each spot and incubated 2 hours in a humidity chamber. The spot was then allowed to dry and was either treated using Calbiochem deglycosylation kit or directly analyzed on SELDI after adding 1 ul of saturated sinapinic acid (Sigma) in 0.5% TFA 50% ACN. The chip was then read on SELDI (Ciphergen) at a Sensitivity=10, Intensity-180-190, range of 0-5000 Da (optimized for 0-5000 Da).

Figure 5A:
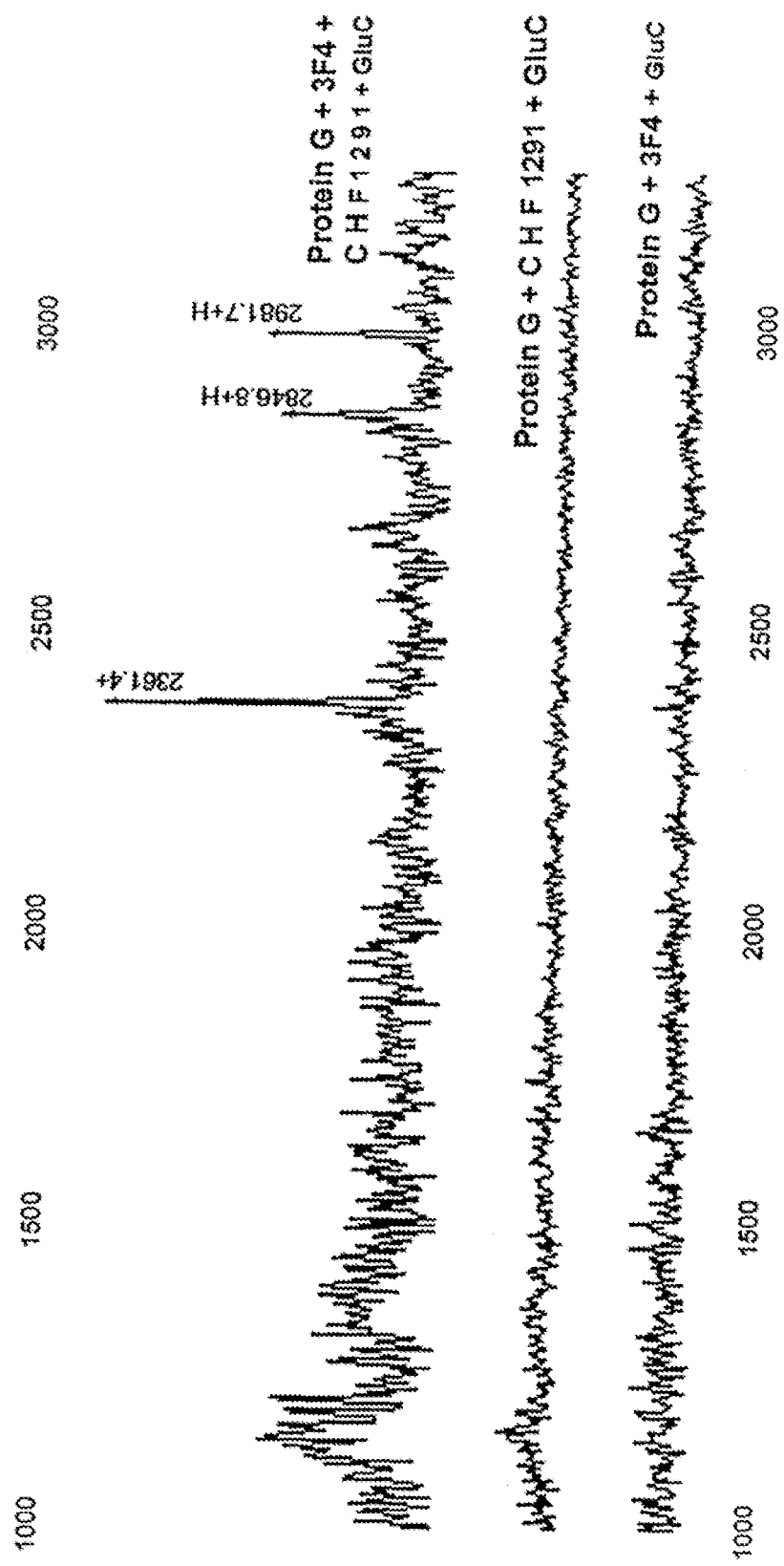
FIGS. 5A-C show chromatograms.
Figure 5B:
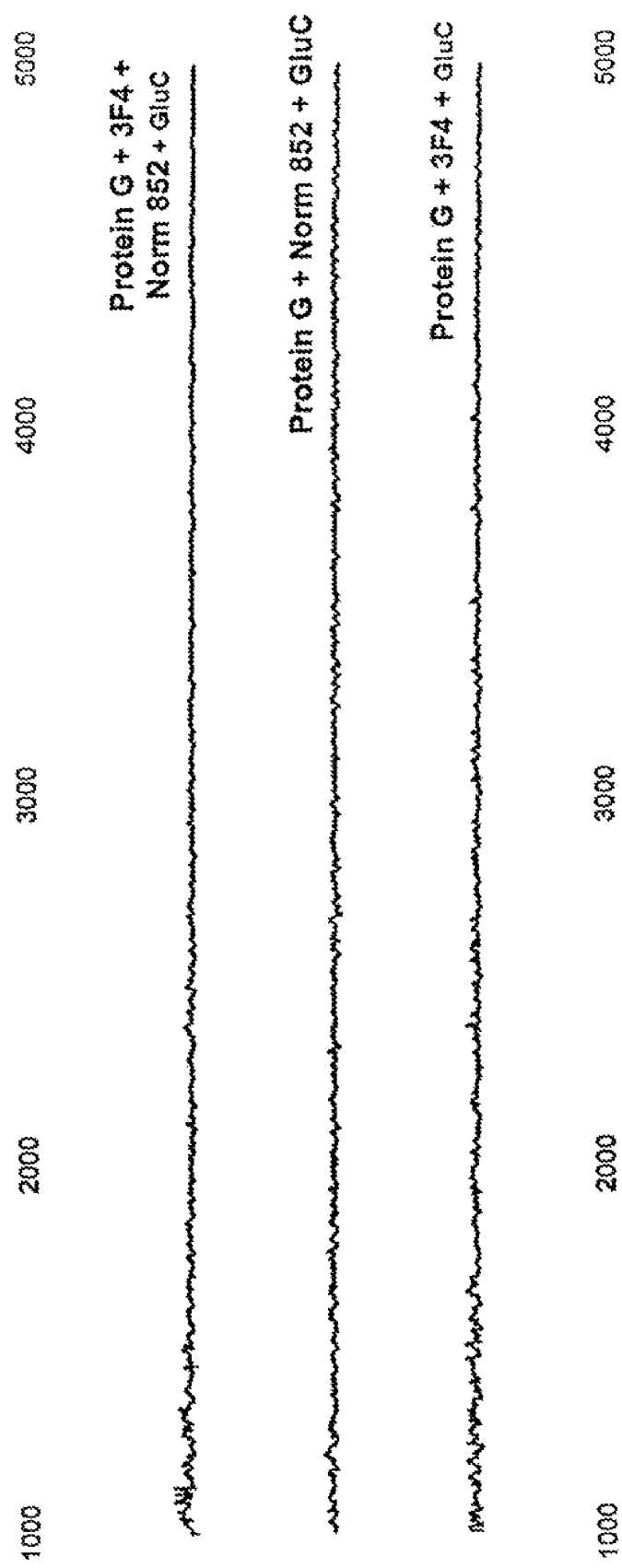
Figure 5C:
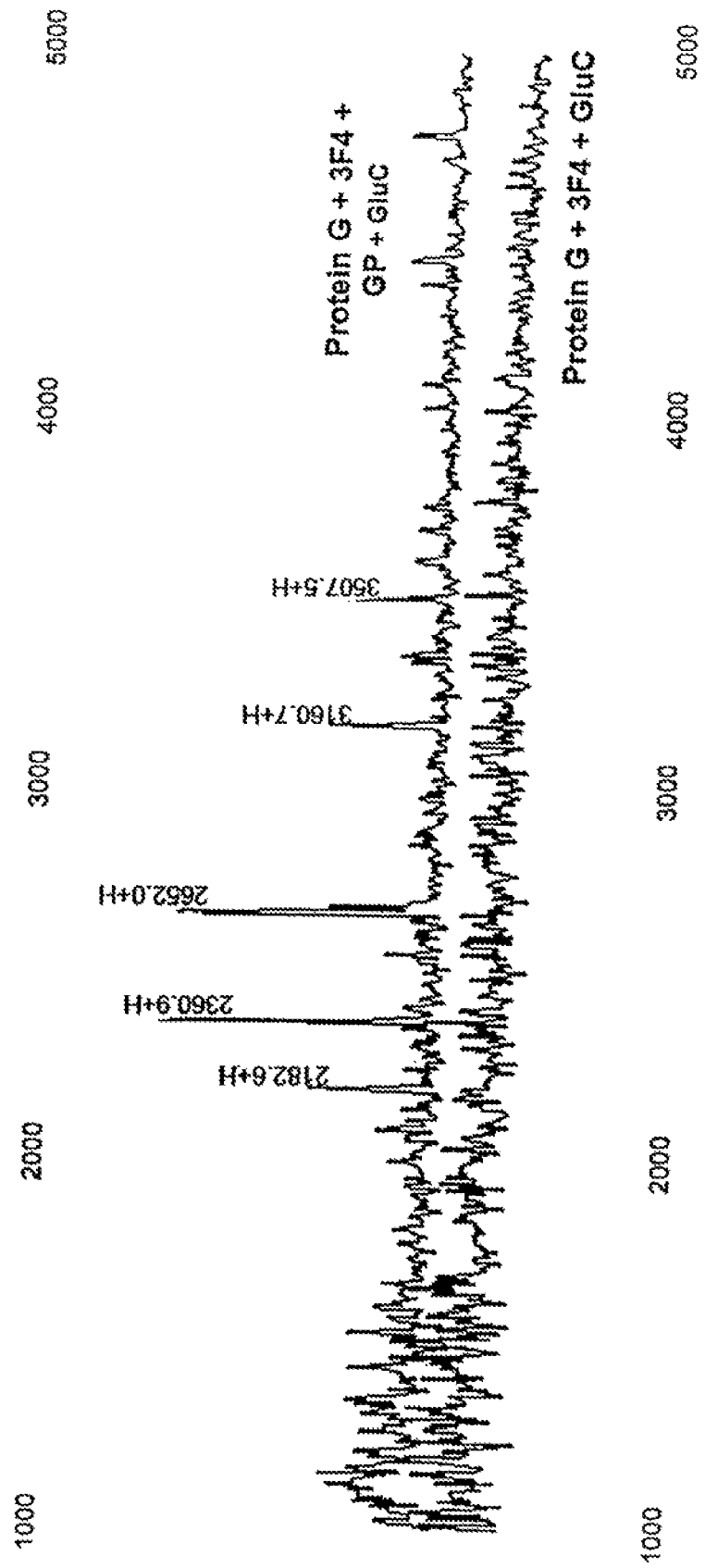

The (glyco)protein captured on the 3F4 chip was treated by GluC. FIG. 5A shows data resulting from the on-chip treatment of the captured glycophorin from CHF. FIG. 5B shows data resulting from the on-chip treatment of the normal plasma samples. FIG. 5C shows data resulting from the on-chip treatment of purified glycophorin. As shown in FIGS. 5A-C, a (glyco)peptide with a m/z of 2361+H is found in both CHF and glycophorin demonstrating that the (glyco)protein captured from CHF corresponds probably to the glycophorin. It is interesting to note that the chromatograms (FIGS. 5A-C) obtained from the purified glycoprhorin and the one from CHF plasma were not overlapped. This is due to the fact that the structure of the glycophorin in CHF is maybe slightly modified.

Figure 6:
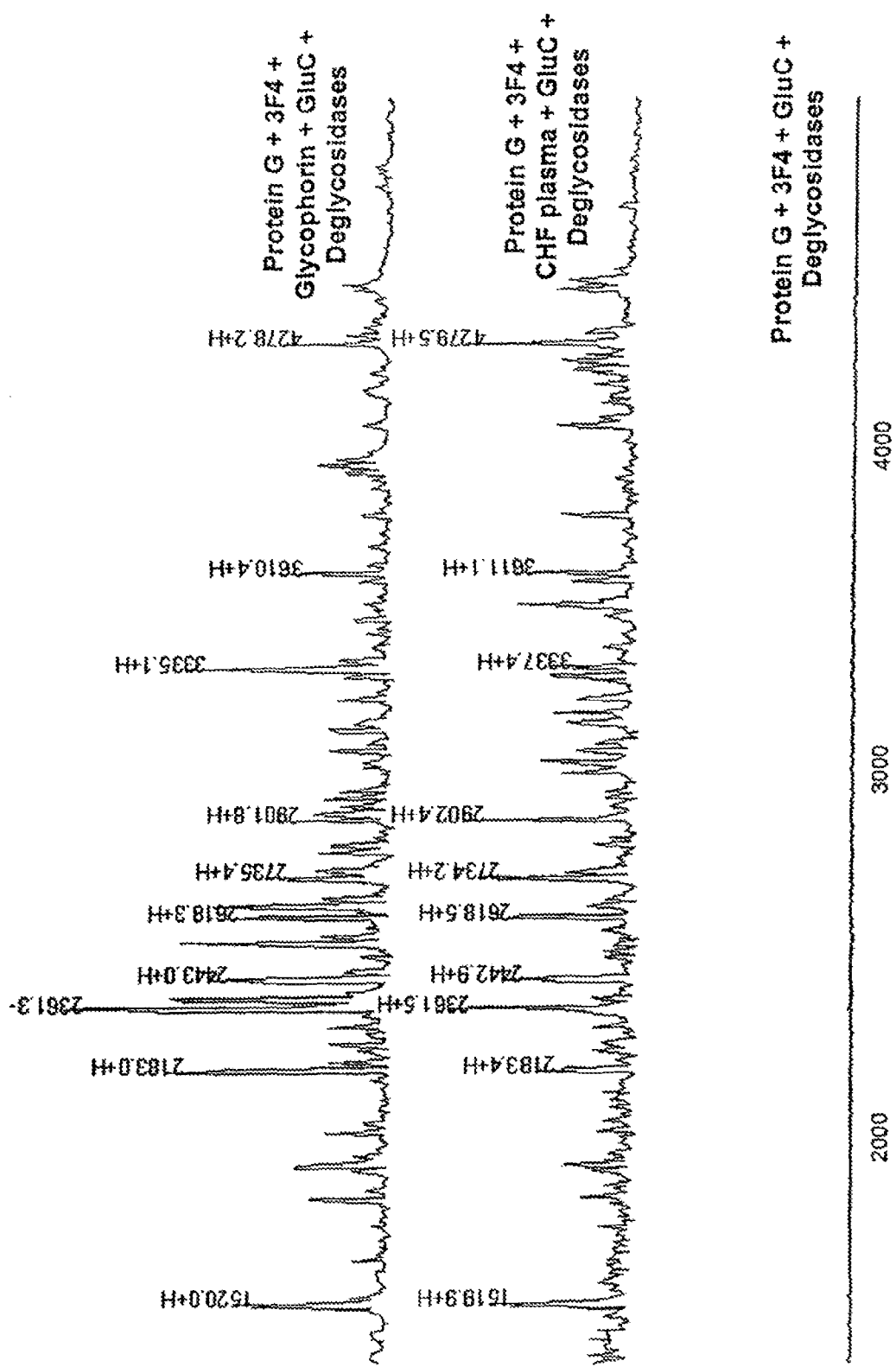
FIG. 6 shows chromatograms after deglycosylation treatment; the top chromatograph shows purified glycophorin; the middle chromatograph shows captured glycophorin from CHF patients and the bottom chromatograph is a control run without a glycophorin sample.

To further prove that the captured (glyco)protein is related to glycophorin, the captured (glyco)protein was deglycosylated on chip. FIG. 6 shows on-chip deglycosylation treatment of the glycopeptides captured from either purified glycophorin or CHF plasma using the 3F4 monoclonal antibody coated on a PS20 chip. As shown in FIG. 6, at least 8 major peaks now matched to the peaks generated from the standard glycophorin. Also, it is noted that a lot more peaks were detected, they correspond not only to the peptides but also to the sugar chains released after the deglycosylation treatment. In conclusion, the instant invention provides a sandwich ELISA assay for quantification of a truncated, glycophorin circulating in biological fluid which is diagnostic for CHF. It is important to note that glycophorin has not been previously recognized as a marker for congestive heart failure (CHF). The instant inventors are the first to document glycophorin as a marker for CHF and the assay described herein provides an efficient, easy to perform diagnostic method capable of identifying an individual suffering from CHF.

All patents and publications mentioned in this specification are indicative of the levels of those skilled in the art to which the instant invention pertains. All patents and publications are herein incorporated by reference to the same extent as if each individual patent and publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. The oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed various modifications of the described modes for carrying out the invention which are obvious to those skilled in the art are intended to be within the scope of the following claims.

What is claimed is:

1. A method for determining whether a subject is suffering from congestive heart failure comprising:
    analyzing a body fluid of the subject to detect a presence and concentration level of unbound and freely circulating truncated glycophorin in said body fluid,
    correlating an elevated level of said truncated glycophorin with congestive heart failure.

2. The method of claim 1, wherein the body fluid is blood plasma.

3. The method of claim 2, wherein the blood plasma is substantially free of red blood cells.

4. The method of claim 1, wherein the glycophorin comprises a circulating, truncated glycophorin.

5. A method for determining whether a subject is suffering from congestive heart failure comprising:
    analyzing a body fluid of the subject to detect a presence and concentration level of an unbound and freely circulating truncated glycophorin recognized by monoclonal antibody 3F4(ATCC PTA-5154); and
    correlating an elevated level of said truncated glycophorin with congestive heart failure.

6. The method of claim 5, wherein said glycophorin is detected immunologically.

7. The method of claim 5, wherein the sample is a plasma sample.

* * * * *

SEQUENCE LISTING

```
<160> NUMBER OF SEQ ID NOS: 4

<210> SEQ ID NO 1
<211> LENGTH: 2593
<212> TYPE: DNA
<213> ORGANISM: Homo sapiens

<400> SEQUENCE: 1
agttgtcttt ggtagttttt tgcactaact tcaggaacca gctcatgatc tcaggatgta        60
```

```
tggaaaaata atctttgtat tactattgtc agcaattgtg agcatatcag catcaagtac      120
cactggtgtg gcaatgcaca cttcaacctc ttcttcagtc acaaagagtt acatctcatc      180
acagacaaat gatacgcaca aacgggacac atatgcagcc actcctagag ctcatgaagt      240
ttcagaaatt tctgttagaa ctgtttaccc tccagaagag gaaaccggag aaagggtaca      300
acttgcccat catttctctg aaccagagat aacactcatt attttggggg tgatggctgg      360
tgttattgga acgatcctct taatttctta cggtattcgc cgactgataa agaaaagccc      420
atctgatgta aaacctctcc cctcacctga cacagacgtg cctttaagtt ctgttgaaat      480
agaaaatcca gagacaagtg atcaatgaga atctgttcac caaaccaaat gtggaaagaa      540
cacaaagaag acataagact tcagtcaagt gaaaaattaa catgtggact ggacactcca      600
ataaattata tacctgccta agttgtacaa tttcagaatg caattttcat tataatgagt      660
tccagtgact caatgatggg gaaaaaaatc tctgctcatt aatatttcaa gataaagaac      720 aaatgttttcc ttgaatgctt gcttttgtgt gttagcataa ttttttagaat tgtttgagaa      780 ttctgatcca aaactttagt tgaattcatc tacgtttgtt taatattaac ttaacctatt      840
ctattgtatt ataatgatga ttctgtcaaa tgaaaggctt gaaataccta gatgaagttt      900
agattttctt cctattgtaa acttttgagt ctggtttcat tgttttaaat aaattaaggg      960
gacactaaag tcctatcatt cattccttca ttctgaacag gcaagatata atattacatg     1020
aatgattact atattttgtt cacactaata aagcttatgc tcagaaatgc catacacaca     1080
cacaaacaca cacatttatc atttaatgca taaatcaaca caaaggtttt tcccattaat     1140
atgaaatatt acatatatat aagtgccata tttaaaataa tttgtctaac agtagaacta     1200
tgtcggagca ctcactgaag cttcgatttc ccactgaaag agttatttgt tgtaagtaga     1260
gttatcccgg agaaggaaaa agaacttacg acctttcttt ataacagaaa gctcaactct     1320
aaattcaaca agatgtgcaa accggacatg caggtgaata ttttaatagg ttactataag     1380
gttctcaatt aaattcttta atctgtccag tcccagtttc tcttattaat aaaactttgg     1440
aaattgcttt aaaccattta aaggaaattt ctagatatag aaactaaagg actgtgacta     1500
tacagtgtca ctcatttgta gtaaaactta aaaagcaaaa acaaaaaaca aaaaagacct     1560
tcctgtgata ctttatttcc gaactaataa aaatctatat gactttttat tattgtgtga     1620
taaccaagta aatgttttct attttcgata ttttcaggca tggtaacaga aatttaccttt    1680 ttaataaatt aaaaaatcta aattttaacc tacttgtatg ttcggagagt gttttttgtac    1740 tatattgact acttaaaata gagaatgaga ctaagaaggg aacatttctg ttgatacatg     1800 tttttttaaaa gtaattttta agagcattat taggttaatt taatccaatt aatgacccaa     1860
atgccaaggt aattttaaat ttacatttt aataaaagca acatgttgaa acaagagagg     1920
gtgagattaa cctttttgct aaagtaattt acaagtcaaa gacaggaaga gatcagagtg     1980
aatgtgcctt cttaaccaga gctacagaat ttagtgaata attaaagtac aaactgctttt   2040 gacctccttg aacttttcca agcaatttct ctgtacttct atatatgaat gtcttagcca     2100
attttctgct actataacag aatacgacag actgggtaat ttaaaaagaa aagaaattta     2160
ttttcttcct agttctggag gctgggaagg cgaagggcat ggcactgaca tctgccttgt     2220
aactgatgag aaccttctta ctgcatgata acaaagcagc aaggcaagca aaagcgtaag     2280
atgaagagag aggaaatgaa gccaaacaca tcctttcatc agaagcccat tccctctata     2340
aggcgttact acatttatga gaatggagtc ctcatgacct aatcgtgacc ttaaaggccc     2400
ctcccaacac tgttacaatg gcaattaaat ttcaacaaag gttccagagg tgacattcga     2460
```

```
atcagcaatg aaattttcat agttaaattt ggtattcgtg ggggaagaaa tgaccatttc    2520
ccttgtattt ttataattaa atcagcaaaa tattgtaata agaaatcttt tcctgtgaag    2580
ataccatgac ccc                                                      2593
```

<210> SEQ ID NO 2
<211> LENGTH: 150
<212> TYPE: PRT
<213> ORGANISM: Homo sapiens

<400> SEQUENCE: 2

```
Met Tyr Gly Lys Ile Ile Phe Val Leu Leu Leu Ser Ala Ile Val Ser
1               5                   10                  15

Ile Ser Ala Ser Ser Thr Thr Gly Val Ala Met His Thr Ser Thr Ser
                20                  25                  30

Ser Ser Val Thr Lys Ser Tyr Ile Ser Ser Gln Thr Asn Asp Thr His
            35                  40                  45

Lys Arg Asp Thr Tyr Ala Ala Thr Pro Arg Ala His Glu Val Ser Glu
        50                  55                  60

Ile Ser Val Arg Thr Val Tyr Pro Pro Glu Glu Glu Thr Gly Glu Arg
65                  70                  75                  80

Val Gln Leu Ala His His Phe Ser Glu Pro Glu Ile Thr Leu Ile Ile
                85                  90                  95

Phe Gly Val Met Ala Gly Val Ile Gly Thr Ile Leu Leu Ile Ser Tyr
                100                 105                 110

Gly Ile Arg Arg Leu Ile Lys Lys Ser Pro Ser Asp Val Lys Pro Leu
            115                 120                 125

Pro Ser Pro Asp Thr Asp Val Pro Leu Ser Ser Val Glu Ile Glu Asn
        130                 135                 140

Pro Glu Thr Ser Asp Gln
145                 150
```

<210> SEQ ID NO 3
<211> LENGTH: 526
<212> TYPE: DNA
<213> ORGANISM: Homo sapiens

<400> SEQUENCE: 3

```
agttgtcttt ggtagttttt ttgcactaac ttcaggaacc agctcatgat ctcaggatgt     60
atggaaaaat aatctttgta ttactattgt cagaaattgt gagcatatca gcattaagta    120
ccactgaggt ggcaatgcac acttcaacct cttcttcagt cacaaagagt acatctcat    180 cacagacaaa tggagaaacg ggacaacttg tccatcgttt cactgtacca gctcctgtag    240
tgataatact cattattttg tgtgtgatgg ctggtattat tggaacgatc ctcttaattt    300
cttacactat tcgccgactg ataaaggcat gaggatgtgg cctgcatgct gcctgtattg    360
cctgcatgct gcctgatctt gcgataaccg gctgcacctg ctgttctctt ctttatgcaa    420
actggctgca cctgctattc ctttgcttat gcccctaccc ctggctatcc taattccctg    480
ttctcctgcc tcactattac tgtattctct acttctaaat aaaaaa                   526
```

<210> SEQ ID NO 4
<211> LENGTH: 91
<212> TYPE: PRT
<213> ORGANISM: Homo sapiens

<400> SEQUENCE: 4

```
Met Tyr Gly Lys Ile Ile Phe Val Leu Leu Leu Ser Glu Ile Val Ser
1               5                   10                  15
```

```
Ile Ser Ala Leu Ser Thr Thr Glu Val Ala Met His Thr Ser Thr Ser
                20                  25                  30

Ser Ser Val Thr Lys Ser Tyr Ile Ser Ser Gln Thr Asn Gly Glu Thr
            35                  40                  45

Gly Gln Leu Val His Arg Phe Thr Val Pro Ala Pro Val Val Ile Ile
        50                  55                  60

Leu Ile Ile Leu Cys Val Met Ala Gly Ile Ile Gly Thr Ile Leu Leu
65                  70                  75                  80

Ile Ser Tyr Thr Ile Arg Arg Leu Ile Lys Ala
                85                  90
```